United States Patent [19]

Graham et al.

[11] Patent Number: 4,961,745
[45] Date of Patent: Oct. 9, 1990

[54] INTRAOCULAR LENS

[75] Inventors: William M. Graham, Vashon, Wash.; Patrice De Laage De Meux, Antibes, France

[73] Assignee: Nestle S.A., Vevey, Switzerland

[21] Appl. No.: 338,611

[22] Filed: Apr. 17, 1989

[51] Int. Cl.⁵ ............................................. A61F 2/16
[52] U.S. Cl. ...................................................... 623/6
[58] Field of Search ............................................. 623/6

[56] References Cited

U.S. PATENT DOCUMENTS

| | | | |
|---|---|---|---|
| 4,280,232 | 7/1981 | Hummel | 623/6 |
| 4,363,143 | 12/1982 | Callahan | 623/6 |
| 4,477,431 | 10/1984 | Kelman | 623/6 |
| 4,579,557 | 4/1986 | Fedorov et al. | 623/6 |
| 4,581,033 | 4/1986 | Callahan | 623/6 |
| 4,711,638 | 12/1987 | Lindstrom | 623/6 |

*Primary Examiner*—Ronald Frinks
*Attorney, Agent, or Firm*—James Arno; Gregg Brown; Sally Yeager

[57] ABSTRACT

An intraocular lens for replacing the natural lens of an eye including a pair of flexible loops connected to and projecting from the optic portion on one side of the first axis, adapted for supporting the IOL in the eye. The loops include outer end portions that terminate outwardly from the peripheral edge and on opposite sides of the second axis. A stabilizing member(s) is connected to and projects from the optic portion on the other side of the first axis from where the loops are connected, adapted for stabilizing the IOL in the eye. The flexible loops and stabilizing member(s) is shaped and dimensioned so that when the loops are moved toward the peripheral edge the outer end portions do not extend beyond the stabilizing member(s).

6 Claims, 2 Drawing Sheets

INTRAOCULAR LENS

FIELD OF THE INVENTION

This invention is in the field of intraocular lenses (IOLs) implantable into an eye after the natural lens of the eye has been removed, as in cataract surgery.

BACKGROUND

The natural lens of an eye can lose transparency and become opaque, forming what is called a cataract. The cataract can vary greatly in size and opacity. If the cataract is large enough and sufficiently opaque to affect vision significantly, it is removed surgically.

Removal can be by means of removing the lens and the capsular bag in which it rests or by removing the lens through the anterior face of the capsular bag, leaving the posterior portion of the bag intact. This latter method is called extracapsular extraction, and it is preferable in many cases because it reduces postoperative complications.

After lens extraction, light entering the eye remains unfocused, causing blurring. A corrective lens can be used to improve vision, with the normally preferred method being implantation of an intraocular lens in the posterior chamber, either between the iris and capsular bag or in the capsular bag. A lens is implanted in a position in the eye where it is centered horizontally and vertically and where it is located in an anterior/posterior location with respect to the remainder of the eye so as to provide optimal vision. Finally, it is desirable to position the lens vertically with respect to the retina, with a minimum of tilting or tipping.

Most IOLs are equipped with thin flexible haptics or support loops which project out from the lens optic for mounting purposes. These haptics are positioned within, and sometimes attached to, the capsular bag to hold the lens in the desired position within the eye. Flexible haptics are generally preferred because they adapt to changes in the shape and size of the eyeball without becoming dislodged or causing trauma to surrounding tissue.

IOLs having thin, flexible haptics are more likely to move slightly away from their desired position than are lenses having stiff haptics. This undesirable dislocation can be in the vertical or horizontal mode, called decentration or tilt, or it can be in the anterior or posterior direction.

An IOL with thin, flexible haptics is also more susceptible to tipping or tilting, which is more likely to be in the anterior direction than in the posterior direction because of the presence of the posterior face of the capsular bag, limiting movement in the posterior direction. An IOL which moves in the anterior direction can in some cases move far enough to be captured by the pupil, resulting in at least temporary loss of vision.

As discussed, there are advantages and disadvantages with both flexible haptics and stiff, flat haptics. Each one has trade-offs against their advantages. It is difficult to produce an IOL which provides adaptability to all conditions in the eye without sacrificing some stability and resistance to decentration and tilting.

SUMMARY OF THE INVENTION

The problems discussed above have been solved by an IOL which is used to replace the natural lens of an eye that includes an optically clear portion having a peripheral edge and including first and second perpendicular axis normal to the peripheral edge. A pair of flexible loops are connected to and project from the optic portion on one side of the first axis. The loops are adapted for supporting the IOL in the eye and include outer end portions that terminate outwardly from the peripheral edge and on opposite sides of the second axis.

The lens further includes a stabilizer connected to and projecting from the optic portion of the side of the first axis opposite where the loops are connected. The stabilizer is adapted for stabilizing the IOL in the eye, with the loops having a length that when they are flexed toward the peripheral edge the outer end portions do not extend beyond the end of the stabilizer.

By providing a stabilizer as described, an IOL that is designed to be placed in the capsular bag can have flexible loops projecting from one side of the optic. However, the IOL will not have a tendency to ride up and down in the bag because the stabilizer remains in contact with the eye on the opposite side of the loops. The stabilizer can be formed in the shape of a single tab connected to the peripheral edge of the optic or to a pair of stabilizer legs providing point contact with the eye.

In this way, a capsular bag lens of a type known in the art has been provided with an improvement for stabilizing and preventing it from moving in the capsular bag in response to normal distortions of the eye ball.

BRIEF DESCRIPTION OF THE DRAWINGS

A better understanding of the invention can be obtained when the detailed description of exemplary embodiments set forth below is considered in conjunction with the appended drawings, in which.

DETAILED DESCRIPTION OF EXEMPLARY EMBODIMENTS

Figure 1:
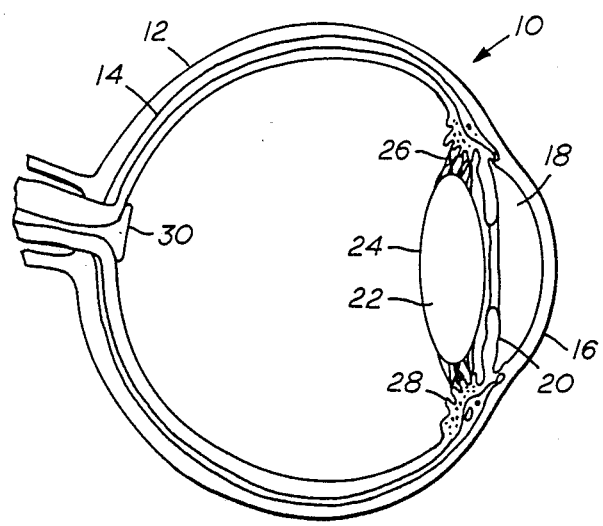
FIG. 1 is a sectional view of a human eye which shows the natural lens intact.

Referring to FIG. 1, a schematic cross-sectional representation of the human eye is designated by reference numeral 10. The eye 10 is made up of an eyeball 12 which is essentially a hollow sphere defined by walls 14 formed of tough but flexible tissue. An image (not shown) is initially received through a cornea 16 and transmitted through an anterior chamber 18 which is located between the inner surface of the cornea 16 and an iris 20 which reacts to the intensity of light and expands or contracts accordingly.

A lens 22 formed of a natural crystalline material is located behind the iris 20 in what is known as the posterior chamber 24 which is the portion of the eye on the rear or posterior side of the iris 20. The lens 22 is held in a membrane called a capsular bag 24 which is connected at its ends through zonular fibers 26 which are in turn connected to the ciliary body 28 of the eye 10. Expansion and contraction of the capsular bag 24 through the interaction of the ciliary body and zonulal fibers cause the lens 22 to change shape and thereby focus light properly on a retina 30 located on the posterior side of the eyeball 12.

Figure 2:
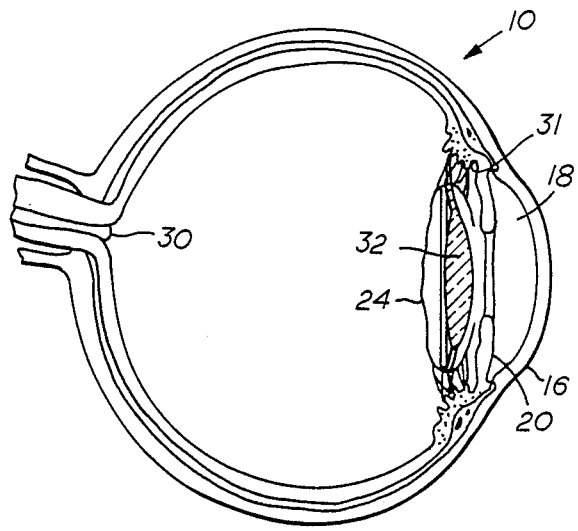
FIG. 2 is a sectional view similar to FIG. 1, but with the natural lens removed and an intraocular lens placed inside the capsular bag.

When the natural lens 22 becomes clouded or other condition prevents light from passing through the lens 22, a condition known as a cataract occurs. An accepted medical procedure for removing a cataract is to penetrate the anterior surface of the capsular bag 24 and remove the crystalline lens 22, leaving the posterior side of the capsular bag intact as shown in FIG. 2. This is done by forming an incision in the cornea 16 and, after dilating the iris 20, surgically puncturing the anterior side of the capsular bag 24 and removing the natural lens 22 either intact or by breaking it up through the use of ultrasonic energy in a process known as phacoemulsification.

After the lens 22 has been removed, a replacement lens known as an intraocular lens (IOL) is inserted through the same incision through which the natural lens is removed. The IOL can be implanted in the anterior chamber directly in front of the iris 20 or in the portion of the posterior chamber between the iris and front portion of the capsular bag in a groove known as the ciliary sulcus 30. Another location can be totally within the capsular bag 24 as shown in FIG. 2. The lens described in detail below is designed to be implanted totally within the capsular bag, although the same principles of design could be used for lenses implanted in other portions of the eye 10.

Figure 3:
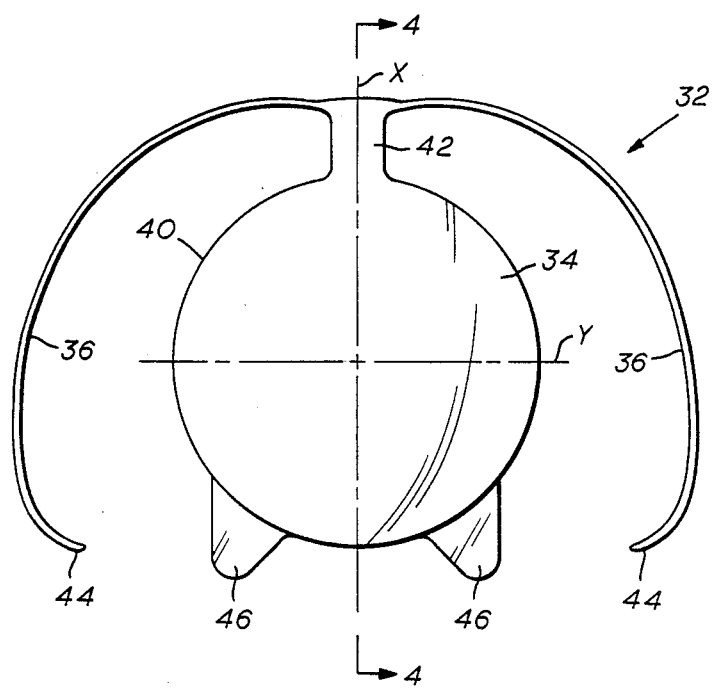
FIG. 3 is a front elevational view of an IOL designed in accordance with the present invention.
Figure 4:
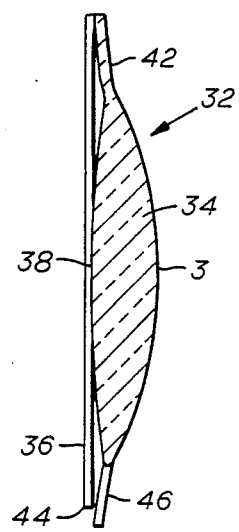
FIG. 4 is a side sectional view looking along the section line 4—4 of FIG. 3.

One embodiment of the lens of the present invention is shown in FIGS. 3 and 4 where an IOL 32 includes an optic portion 34 and a pair of flexible loops or haptics 36. The optic 34 has convex anterior and posterior surfaces 36, 38, respectively, and is therefore known as a bi-convex optic. The optic in the plane normal to the peripheral edge 40 of the optic has, by way of reference, a vertical axis X and horizontal axis Y.

The flexible loops 36 are connected to the optic 34 through a tab 42 formed integral with the peripheral edge 40 on one side of the axis Y. The loops 36 are formed integral with and project from opposite sides of the tab 42 in a sweeping and generally concentric configuration relative to the peripheral edge 40 and terminate at outer end portions 44.

A pair of stabilizer tabs 46 are integrally connected with the peripheral edge 40 on the side of the axis Y opposite the tab 42. The stabilizer tabs 46 project outwardly from the peripheral edge 40 and operate to hold that portion of the IOL 32 in place in the capsular bag 24. As shown diagrammically by the broken lines in FIG. 5, the loops 36 and stabilizer tabs 46 are sized and shaped so that when the loops 36 are flexed inwardly toward the peripheral edge 40 (see the broken lines in FIG. 5) the outer end portions 44 do not project beyond the outer ends of the stabilizer tabs 46. This provides a smooth transition of contact of the flexible loops 36 and stabilizer tabs 46 in the capsular bag.

It can be seen that the supporting loops 36 operate to support the IOL 32 in the capsular bag, while the stabilizer tabs 46 stabilize the portion of the optic 34 on the opposite sides of where the loops 36 are attached and prevent the optic from moving down or decentrating in the eye or moving in an anterior-posterior direction which would result in tilting of the lens.

The IOL 32 can be formed of any suitable optically-clear and bio-compatible plastic such as polymethylmethacrylate (PMMA). The IOL 32 can be formed of a single piece of PMMA that is either lathe cut or cast or it can be formed of multiple pieces of bio-compatible material that are joined together in an appropriate manner. The diameter of the optic portion can be 7 mm and the distance between the outer edges of the support loops 36 in the unflexed position shown in FIG. 3 can be 13 mm and in the compressed position shown by the broken lines in FIG. 5, 10 mm. This 10 mm distance can also represent the circumference of the outer ends of the tab 42 and the stabilizer tabs 46.

As shown in FIG. 4, the tab 42 and stabilizer tabs 46 can be formed at an angle A relative to the vertical axis of the optic 34, preferably about 8°, so that the loops 36 can be offset from the posterior side 38 of the optic 34. This operates to project the optic closer to the iris 20 and out of contact with the posterior side of the capsular bar 24.

Figure 5:
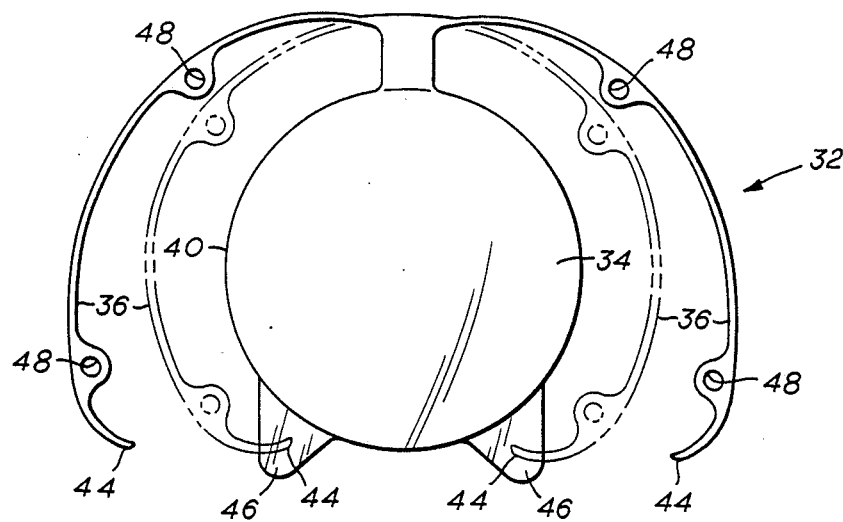
FIG. 5 is a front elevational view of an IOL similar to the one shown in FIG. 3, but with positioning holes located on the loops and with broken lines showing the location of the loops when they are flexed inwardly toward the optic.
Figure 6:
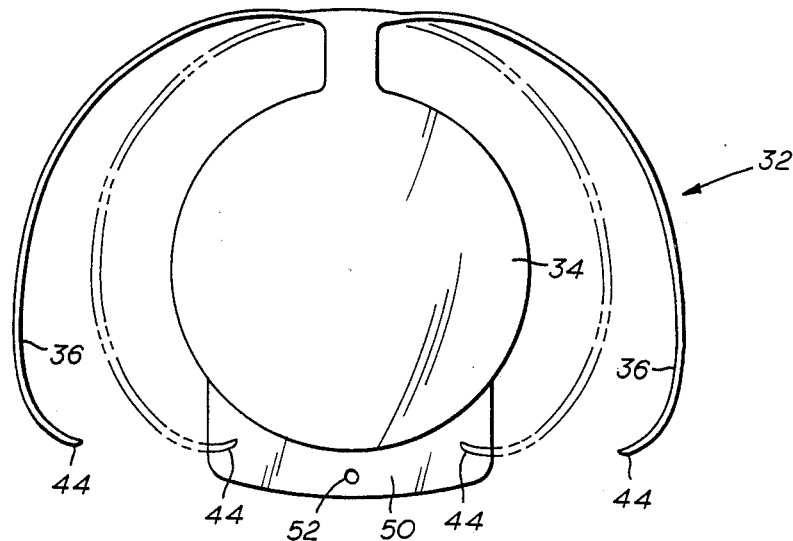
FIG. 6 is a front elevational view of another embodiment of the IOL of the present invention where the stabilizer is in the form of a solid tab projecting from the optic, with the broken lines showing the position of the flexible loops when they are flexed toward the optic.

The IOL 32 can include a pair of suture fixation holes 48 spaced apart on each loop 36 as shown in FIG. 5. As shown in FIG. 6, a stabilizer tab 50 extending across the optic portion 34 can be used in place of the pair of stabilizing tabs 46 shown in FIG. 5. As shown, the stabilizer tab 50 could be provided with a positioning hole 52 to help a surgeon in the manipulation of the IOL 32 during implantation. Also as shown in FIG. 6 by the representation of the loop 36 shown in the broken lines, when the loops are flexed inwardly toward the optic 34, the outer end portions 44 do not extend beyond the outer edge of the stabilizer tab 50 for the reasons mentioned above.

Therefore, an IOL is described and shown that solves the problems discussed above of decentration and tilting of lenses of a particular haptic or loop design which are used for implantation in the capsular bag. These problems are solved by providing a stabilizer on the optic portion on the side opposite where the loops or haptics are attached to prevent the lens from moving up and down in the eye and to prevent the bottom portion of the portion from moving in the anterior-posterior direction.

The description of the invention set forth above is intended to be exemplary and not limiting. One with ordinary skill in the art would be able to make improvements, variations and modifications without departing from the spirit and scope of the invention. All such improvements, variations and modifications are intended to be included within the scope of the appended claims.

I claim:

1. An intraocular lens for replacing the natural lens of an eye, comprising:
   (a) an optically-clear optic portion having a peripheral edge and first and second perpendicular axes normal to the peripheral edge;
   (b) a pair of flexible loops connected to a connection tab connected to and projecting outwardly from the optic portion on one side of the first axis, adapted for supporting the IOL in the eye, the loops including outer end portions that terminate outwardly from the peripheral edge and on opposite sides of the second axis;

(c) stabilizer means connected to and projecting from the optic portion on the other side of the first axis from where the loops are connected, adapted for stabilizing the IOL in the eye; and (d) the flexible loops and stabilizing means being shaped and dimensioned so that when the loops are moved toward the peripheral edge the outer end portions do not extend beyond the stabilizing means.

2. The intraocular lens of claim 1, wherein each flexible loop curves in an arc substantially concentric with the optic portion.

3. The intraocular lens of claim 1, wherein each flexible loop includes at least one hole located along its length for enabling the lens to be sutured to tissue in the eye.

4. The intraocular lens of claim 1, wherein the stabilizing means is generally in the shape of a pair of triangular tips connected to the periphery of the optic portion.

5. The intraocular lens of claim 1, wherein the stabilizer means is in the shape of a single flange extending along a portion of the periphery of the optic portion.

6. The intraocular lens of claim 1 wherein the connection tab is oriented at an angle relative to the plane of the optic portion.

* * * * *